United States Patent
Ross

[11] 4,207,107
[45] Jun. 10, 1980

[54] NOVEL ORTHO-QUINONE DIAZIDE PHOTORESIST SENSITIZERS

[75] Inventor: Daniel L. Ross, Princeton, N.J.

[73] Assignee: RCA Corporation, New York, N.Y.

[21] Appl. No.: 936,038

[22] Filed: Aug. 23, 1978

[51] Int. Cl.² .................. G03C 5/00; G03C 1/52; C07C 113/00
[52] U.S. Cl. .................. 430/165; 260/141; 260/146 D; 260/155; 546/100; 430/193; 430/270; 430/586
[58] Field of Search .............. 260/141 D, 155, 146 D; 96/91 D, 115 R, 36, 49

[56] References Cited

U.S. PATENT DOCUMENTS

| | | | |
|---|---|---|---|
| 2,961,438 | 11/1960 | Fuchs et al. | 260/152 |
| 3,046,118 | 7/1962 | Schmidt | 96/49 |
| 3,852,771 | 12/1974 | Ross | 96/91 D |

OTHER PUBLICATIONS

Cason, et al., "Synthesis of Four Methoxy-Substituted 1,8-Naphthalic Anhydrides", J. Org. Chem., vol. 33, pp. 3404–3408, 1968).

*Primary Examiner*—Won H. Louie, Jr.
*Attorney, Agent, or Firm*—Birgit E. Morris; Edward J. Sites

[57] ABSTRACT

Ortho-quinone diazide compounds of the formula

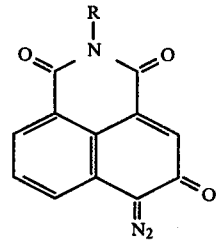

wherein R is an organic radical are useful sensitizers for photoresist compositions and intermediates for novel dyes.

12 Claims, 1 Drawing Figure

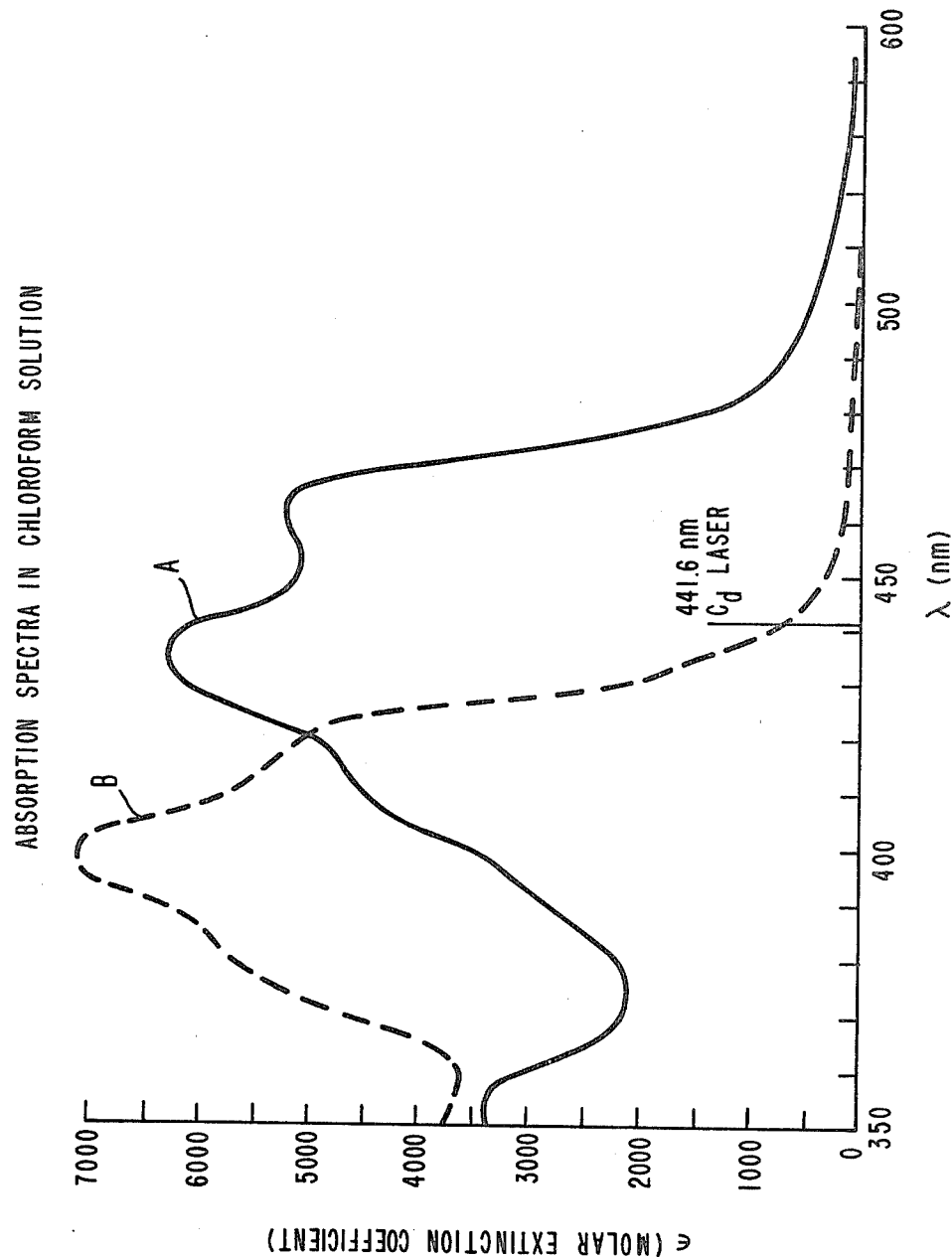

1

NOVEL ORTHO-QUINONE DIAZIDE PHOTORESIST SENSITIZERS

This invention relates to novel ortho diazo ketones derived from 1,8-naphthalimides useful as precursors for dyes and photosensitizers for photoresists.

BACKGROUND OF THE INVENTION

Certain ortho-quinone diazides such as 2-diazo-1-naphthol-5-sulfonic acid and the -4-sulfonic acid, having the formulas

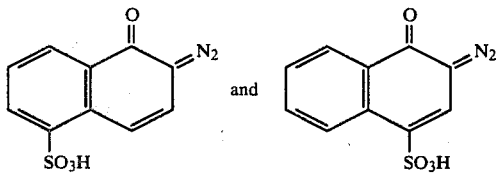

and respectively, are useful commercially as precursors for their corresponding sulfonamides and esters which are used as sensitizers for photoresists and electron beam resists; see for example U.S. Pat. Nos. 3,046,118 and 3,852,771. Each class of photoresists has an absorption maximum at a certain wavelength region. The above light sensitive compounds absorb in the near ultraviolet region at about 400 nanometers wavelength or below and have very little absorption beyond about 450 nanometers. It would be desirable to expand the region of absorptivity of photoresists to longer wavelengths, particularly because the common lasers used for high resolution recording and holography are the argon ion laser, which can emit at about 488 nanometers, and the helium-cadmium laser which can emit at 441.6 nanometers.

BRIEF DESCRIPTION OF THE DRAWING

The FIGURE is a graph of the absorption spectrum of a compound of the invention and a control compound.

SUMMARY OF THE INVENTION

I have found novel ortho-quinone diazide compounds of the formula

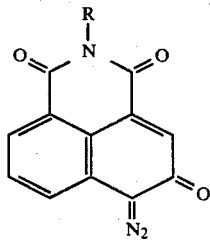

wherein R is an organic radical, that are light sensitive and absorb light at longer wavelengths than conventional ortho-quinone diazide compounds. These compounds are useful as sensitizers for photoresist compositions and as intermediates for the preparation of novel dyestuffs.

DETAILED DESCRIPTION OF THE INVENTION

The ortho-quinone diazide compounds of the invention can be readily prepared from naphthalic anhydride in a series of reactions; first, reacting with sulfuric acid forming the 3-sulfonic acid derivative; second, converting that to its corresponding 3-hydroxy derivative; thirdly, reacting with nitric acid to form the 3-hydroxy-4-nitro compound; fourth, reacting with a primary amine to form the imine; fifth, hydrogenating the imine to convert the nitro group to the amine group; and, sixth and last, reacting with nitrite and cupric ion to form the naphthalimide compound. The above series of reactions are summarized in the scheme set forth below:

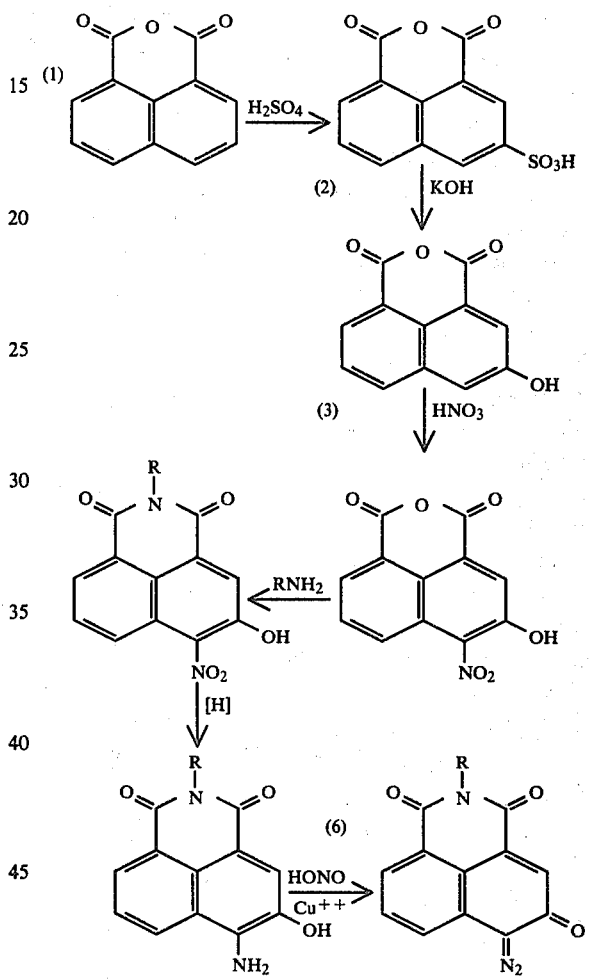

As an alternative, the 3-hydroxy-4-nitro compound can be reduced to the aminohydroxy anhydride and reacted with a primary amine to give the naphthalimide compound.

The primary amine determines the "R" group in the above general formula (1). The organic radical represented by R can include aliphatic groups, such as an alkyl, alkoxy, ether or alicyclic group and the like, aromatic groups such as o, m, or p-substituted phenyl, naphthyl or anthryl and the like; heterocyclic groups wherein atoms such as N, S or O are present in an aliphatic or aromatic ring; and polymeric residues of polymers having pendant —$NH_2$ groups.

In addition, carboxylic or sulfonic acid-terminated or acid chloride terminated "R" groups, which in turn can be reacted to form carboxylic esters and amides, can also be made by appropriate reactions of the "R" group. These reactions can be performed either after reaction with the primary amine to form the imine (equation 4 above) or with the compounds of the invention. As illustrations, the "R" group can be A—COOX or A—SO₃X wherein A is alkylene or arylene and X is an aliphatic or aryl group, or A—CONYX or A—SO₂NYX wherein A and X are as defined above and Y is hydrogen, alkyl or aryl. These terminal X groups can also be reacted with appropriate hydroxy- or amino-terminated polymers.

The compounds of the invention absorb light generally in the region from about 400 to about 550 nanometers wavelength, which encompasses the region of emission of both the helium-cadmium and argon ion lasers.

The light sensitive compounds of the invention can be admixed with an alkali soluble resin, such as a novolak resin, a cellulose derivative, a homopolymer or copolymer of vinyl acetate or the like. The preferred resins are novolaks prepared from phenols and aldehydes, most preferably a cresol-formaldehyde resin. The mixture of resin and light sensitizer is dissolved in a suitable organic solvent in known manner to form a photoresist composition. Generally about 5 to about 50 weight percent of the light sensitive compound in the alkali soluble resin based on the weight of the mixture will be used.

The photoresist is applied in known manner, as by dipping, spraying, spinning and the like onto a substrate. The photoresist can be exposed to an information carrying light beam, as to a modulated light beam, such as from a helium-cadmium or argon ion laser, or using flood illumination through a mask, and developed with a basic solution, such as an alkali metal hydroxide solution, to form a relief pattern.

The compounds of the invention are also useful as intermediates in the preparation of azo dyes analogous to conventional azo dye materials of the general formula

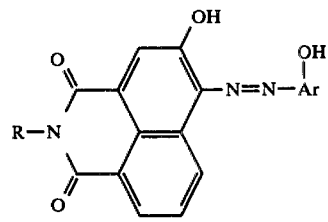

wherein R is an organic radical and Ar is an aryl group, such as phenyl or naphthyl, substituted in the ortho position with the hydroxyl group and which can be further substituted with a halogen, or carboxy or sulfonic acid group and derivatives thereof. For example, the compounds of the invention can be reacted with p-naphthol to form the corresponding azo dyes, as shown in the equation below:

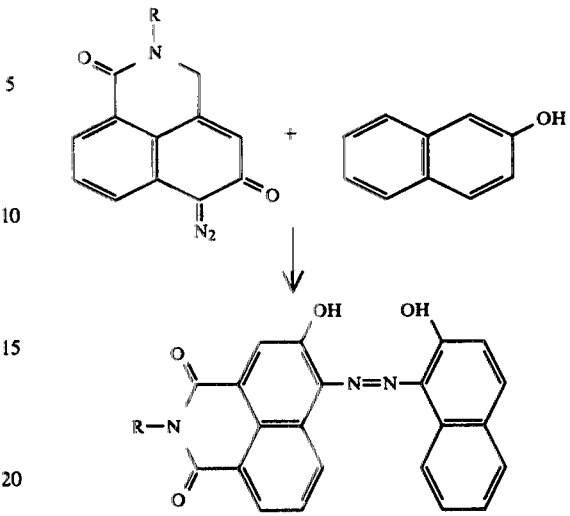

wherein R is as defined above. Such diazo dyes can be further reacted to form light stable metal complexes of the formula

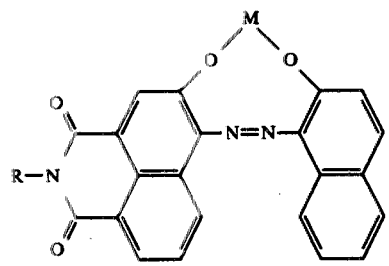

wherein M represents a metal.

The invention will be illustrated further by the following Examples, but the invention is not meant to be limited to the details described therein. In the Examples, parts are by weight unless otherwise noted.

EXAMPLE 1

Part A: Preparation of 3-sulfo-1,8-naphthalic anhydride

A solution containing 50 parts of 1,8-naphthalic anhydride, 150 parts of 20–23 percent and 150 parts of 30–33 percent fuming sulfuric acid was stirred for 30 minutes at 90°–95° C. After cooling to room temperature, the solution was poured into 350 parts of crushed ice and cooled to 15° C. The precipitate was collected by filtration, washed first with glacial acetic acid and then with hexane and dried under vacuum.

69.5 Parts of 3-sulfo-1,8-naphthalic anhydride of the formula

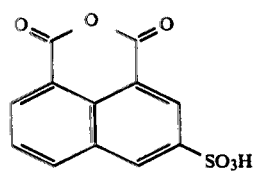

was obtained.

Part B: Preparation of 3-hydroxy-1,8-naphthalic anhydride

30 Parts of the product of Part A was added portionwise while stirring to a mixture of 150 parts of potassium hydroxide and 4.5 parts of water at 180° C. The mixture was stirred at 220° C. for 15 minutes, cooled to room temperature and dissolved in 300 parts of water. The mixture was acidified to a pH of 8 with concentrated hydrochloric acid and filtered. An additional 250 parts of concentrated hydrochloric acid was added, the mixture was heated to boiling and cooled overnight. The precipitate was collected by filtration, washed with water, dried and recrystallized from ethanol.

A yield of 63 percent (14.5 parts) of 3-hydroxy-1,8-naphthalic anhydride was obtained as a yellow solid of the formula

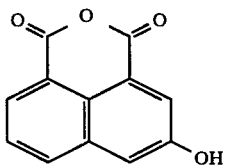

The product had a melting point of 285°–287° C.

Part C: Preparation of 3-hydroxy-4-nitro-1,8-naphthalic anhydride

3-Hydroxy-4-nitro-1,8-naphthalic anhydride was prepared from the product of Part B following the procedure in Journal of Organic Chemistry, Volume 33, page 3404 (1968). A yield of 62 percent was obtained.

The product has the formula

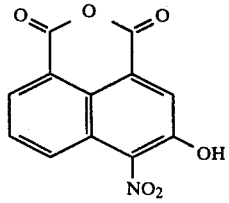

Part D: Preparation of N-(p[2'-pentyl])phenyl-3-hydroxy-4-nitro-1,8-naphthalimide The product obtained from Part C and an equivalent amount of 4-(2'-pentyl)aniline was added to acetic acid, refluxed for 5 hours and cooled to room temperature. The precipitate was collected, washed with acetic acid and hexane and dried.

A yield of 62 percent of a yellow, crystalline product of the formula

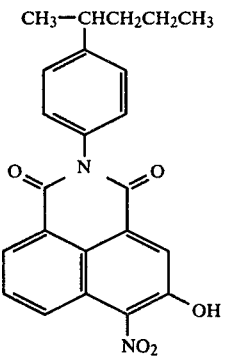

was obtained. The product was recrystallized from methanol.

Part E: The preparation of N-(p[2'-pentyl])phenyl-4-amino-3-hydroxy-1,8-naphthalimide hydrochloride The product of Part B was hydrogenated using a 10 percent palladium on carbon catalyst in a 30:70 dioxane/ethanol solvent in a Parr apparatus at 35 psig. pressure. When hydrogen takeup ceased, a slight excess of concentrated hydrochloric acid and ethanol were added, the mixture was heated to boiling, and filtered. The solvent was removed by evaporation.

A 91 percent yield of the product having the formula

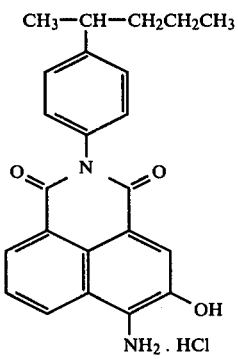

was obtained.

Part F: Preparation of N-(p-[2'-pentyl])phenyl-4-diazo-3,4-dihydro-3-oxo-1,8-naphthalimide To 1.01 parts of the hydrochloride salt of the product of Part E dissolved in 25 parts by volume of ethanol, 0.5 part of water and 0.9 part of 10 percent hydrochloric acid, was added 0.06 part of cupric acetate hydrate. The mixture was cooled to 15° C. and a solution containing 0.17 part of sodium nitrite was added dropwise while stirring. After all of the nitrite was added, the mixture was stirred for 10 minutes, 30 parts of water were added and the precipitate collected by filtration and dried.

A yield of 98 percent (0.92 part) of the product having the formula

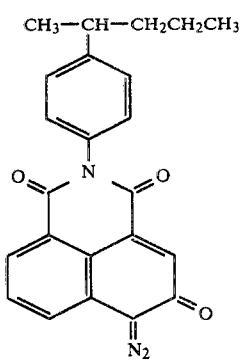

was obtained as a brownish yellow powder. The product was recrystallized from 1:2 chloroform/methanol to obtain gold crystals which darken at 150° C. and decompose without melting at 205°–215° C.

Part G

A $1\times10^{-4}$ molar solution of the product of Part F in chloroform was made and its absorption spectrum determined. Curve A in the FIGURE shows an absorption maximum at about 438 nanometers, which is near the emission line of the helium-cadmium laser (441.6 nm).

Curve B of the FIGURE shows an absorption spectrum of a chloroform solution of like concentration of N-(n-dodecyl)-6-diazo-5,6-dihydro-5-oxo-1-naphthalene sulfonamide which has the formula

This material has an absorption maximum at about 395 nanometers.

EXAMPLE 2

Part A: Preparation of
N-3'(2"-methoxyethoxy)propyl-3
hydroxy-4-nitro-1,8-naphthalimide Equimolar amounts of 3-hydroxy-4-nitro-1,8-naphthalic anhydride obtained as in Example 1, Part C and 3-(2'-methoxyethoxy) propyl amine in pyridine were refluxed for 3 hours. The mixture was then cooled and poured over an ice-hydrochloric acid mixture. A brown oil separated and was allowed to solidify overnight. The product was purified by crystallizing from carbon tetrachloride, chromatographed on silica gel using methanol-chloroform as elutant and recrystallized from benzene.

The product having the formula

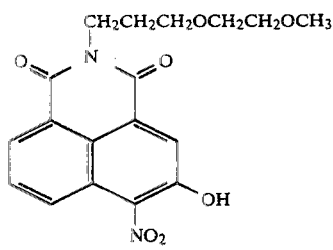

was obtained as a yellow solid having a melting point of 124°–125.5° C.

Part B: Preparation of
N-3'(2"methoxyethoxy)propyl-4-amino
3-hydroxy-1,8-naphthalimide hydrochloride The product of Part A was hydrogenated as in Example 1, Part E using a 15:85 dioxane-ethanol mixture. When hydrogen uptake ceased, the mixture was filtered into a mixture of concentrated hydrochloric acid and ethanol. The solvent was removed to form a quantitative yield of the salt

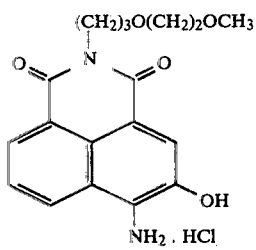

Part C: Preparation of
N-3'(2"-methoxyethoxy)propyl-4-diazo-3,4-dihydro-3-oxo-1,8-naphthalimide A suspension was prepared of 2.44 parts of the salt prepared as in Part B in 63 parts of water and 8.4 parts by volume of 10 percent hydrochloric acid. Cupric acetate hydrate (0.165 part) was added, the mixture stirred and cooled to 15° C. and a solution of 0.457 part of sodium nitrite in 2.5 parts of water added dropwise, forming a solution. The reaction mixture was stirred for 15 minutes and extracted with four 50 part portions of chloroform. The extracts were combined, dried over anhydrous sodium sulfate and the solvent removed. The residue was purified by dissolving in ethyl acetate and filtering through neutral alumina. The solvent was removed to yield a crude product which was recrystallized from carbon tetrachloride/cyclohexane.

A yield of 44 percent (1.04 parts) of product having the formula

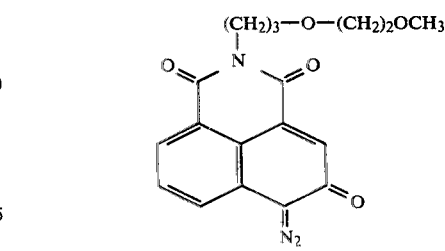

and a melting point of 98°–101° C. was obtained.

Elemental analysis was; theoretical: 60.8 percent C, 4.82 percent H, 11.8 percent N. Found: 61.0 percent C, 4.89 percent H, 12.6 percent N.

EXAMPLE 3

Thirteen parts of the product of Example 1 were added to a 15 percent solution of 87 parts of a cresolformaldehyde novolak resin in 2-methoxyethyl acetate. The resulting photoresist solution was applied by spinning onto an aluminum coated glass slide to form a 1 micron thick layer. A portion of the slide was given a 10 millijoules/cm$^2$ exposure to a light beam from a helium-cadmium laser. The photoresist was developed by immersing in a stirred developer solution of 1 part of the Shipley Co.'s AZ-303 developer in 6 parts of water. A surface relief pattern about 100 microns deep was obtained.

I claim:

1. A compound which absorbs light in the range of about 400 to about 500 nanometers wavelength, of the formula

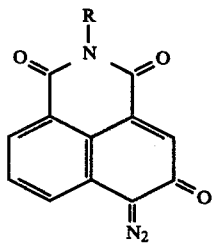

wherein R is an organic radical.

2. A compound of the formula

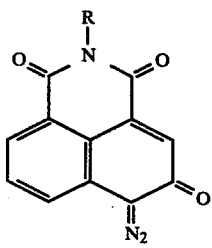

wherein R is a member of the group consisting of —ACOOX, —ASO$_3$X, —ACONYX and —ASO$_2$NYX wherein A is arylene, X is an aliphatic or aryl group and Y is hydrogen, alkyl or aryl.

3. The compound according to claim 1 wherein R is a residue of a polymer having a pendant —NH$_2$ group.

4. A compound of the formula

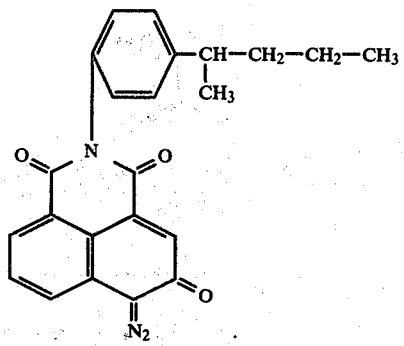

5. A compound of the formula

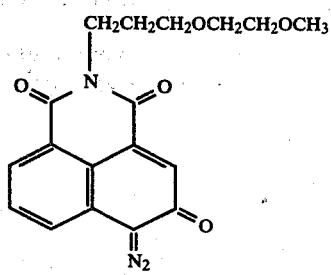

6. A photoresist composition comprising a mixture of an alkali soluble resin and a sensitizer compound which absorbs light in the range of about 400 to about 500 nanometers wavelength, of the formula

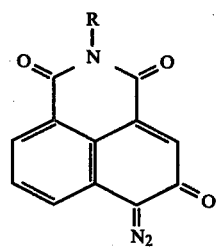

wherein R is an organic radical.

7. A photoresist composition according to claim 6 wherein the sensitizer compound comprises from about 5 to 50 percent by weight of said mixture.

8. In a method of recording information whereby a light sensitive material layer is exposed to an information-carrying light beam whereby the light sensitive material becomes more soluble in a developer solvent when impinged upon by light and the light sensitive material is developed with the developer solvent so as to remove the solubilized portion, the improvement which comprises employing as said light sensitive material a mixture of (a) a light sensitizer which absorbs light in the range of about 400 to 500 nanometers wavelength, having the formula

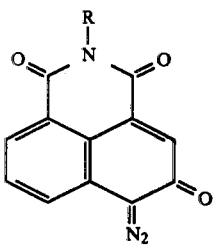

wherein R is an organic radical and (b) an alkali soluble resin.

9. A method according to claim 8 wherein said alkali sensitive resin is selected from the group consisting of novolaks, cellulose derivatives and homopolymers and copolymers of vinyl acetate.

10. A method according to claim 9 wherein said resin is a novolak resin.

11. A method according to claim 8 wherein said mixture contains from 5 to 50 percent by weight of said light sensitizer.

12. A compound of the formula

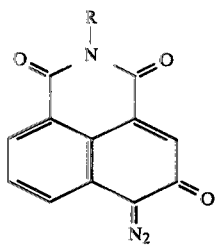

wherein R is an organic radical selected from the group consisting of alkyl, alkoxy, aliphatic ether, alicyclic, o, m, or p-substituted phenyl, o, m, or p-substituted naphthyl, o, m, or p-substituted anthryl, an aliphatic moiety having N, S, or O in its ring, an aromatic moiety having N, S, or O in its ring, a polymeric residue of a polymer having a pendant —$NH_2$ group, and a moiety of the formula —ACOOX, —$ASO_3X$, —ACONYX or —$ASO_2NYX$ where A is arylene, X is an aliphatic or aryl radical and Y is hydrogen, alkyl or aryl.

* * * * *